(12) United States Patent
Powers et al.

(10) Patent No.: US 7,651,477 B2
(45) Date of Patent: Jan. 26, 2010

(54) CANNULA HAVING UNBREAKABLE TIP

(76) Inventors: David M. Powers, 9 Park Dr., Menands, NY (US) 12204; Gary Van Meer, 2997 Post Rock Ct., Tarpon Springs, FL (US) 34688

( * ) Notice: Subject to any disclaimer, the term of this patent is extended or adjusted under 35 U.S.C. 154(b) by 380 days.

(21) Appl. No.: 11/680,254

(22) Filed: Feb. 28, 2007

(65) Prior Publication Data
US 2008/0208131 A1     Aug. 28, 2008

(51) Int. Cl.
*A61M 5/178* (2006.01)
(52) U.S. Cl. .................................. 604/164.11
(58) Field of Classification Search ............ 604/164.11, 604/273, 525, 164.1
See application file for complete search history.

(56) References Cited
U.S. PATENT DOCUMENTS 5,256,149 A  * 10/1993  Banik et al. ............ 604/164.01
5,389,077 A  *  2/1995  Melinyshyn et al. ........ 604/117
5,533,988 A  *  7/1996  Dickerson et al. ............ 604/523
5,824,002 A  * 10/1998  Gentelia et al. ........ 604/164.11
2007/0149927 A1*  6/2007  Itou et al. .................... 604/158

* cited by examiner

*Primary Examiner*—Nicholas D Lucchesi
*Assistant Examiner*—Brooke M Matney
(74) *Attorney, Agent, or Firm*—Ronald E. Smith; Smith & Hopen, P.A.

(57) ABSTRACT

A cannula includes an elongate cannula body formed of a translucent polycarbonate plastic having a distal end and the distal end has a sharp edge that frays and weakens sutures that rub against it. A distal tip has a rounded leading end and is disposed in overlying, protective relation to the distal end of the cannula body and the sharp edge. The distal tip is formed of a material that is substantially unbreakable upon contact with bone or other hard material encountered during surgery. The material may be a metal, a thermoplastic urethane or a thermoplastic urethane rubber. An annular recess formed in a lumen of the cannula body at the distal end of the cannula body accommodates the distal tip so that the lumen of the cannular body and the lumen of the distal tip are flush with one another.

5 Claims, 2 Drawing Sheets

CANNULA HAVING UNBREAKABLE TIP

BACKGROUND OF THE INVENTION

1. Field of the Invention

This invention relates to surgical instruments. More particularly, it relates to a cannula having a tip that does not break or chip when used in a surgical procedure.

2. Description of the Prior Art

An anchor is an implant used in orthopedic surgery. It is screwed into a humeral head by a surgeon performing a rotator cuff repair or into the glenoid if performing a labral repair.

Cannulas are commonly used in arthroscopic surgery. The distal end of a conventional cannula terminates in a tip having a sharp inner edge. When a suture is used, it can rub against such sharp inner edge. Such rubbing frays the suture and reduces its strength. The rubbing can also cause the suture to break. If the suture is secured to an anchor, the patient is charged for an additional suture and a new anchor. Depending upon the manufacturer, an anchor to repair a rotator cuff or labrum ranges from $150.00 to $400.00. When the suture of an anchor breaks, another anchor needs to be opened to complete the repair. This causes an additional cost to the hospital and the patient.

Moreover, the replacement anchor will not be as ideally positioned as the first, no-longer-usable anchor because the surgeon will have positioned the first anchor in an optimal location. The second anchor will thus be positioned in a second-best location.

Thus there is a need for a cannula that does not have a sharp inner edge at its distal end so that sutures are not frayed or broken by said cannula and so that a need for a second anchor will not arise.

Conventional cannulas are also subject to breakage at their distal tip. Breakage may occur if a surgeon hits a bone with sufficient force to cause such breakage. Introducing an orthopedic instrument into the lumen of the cannula during arthroscopic repair of a rotator cuff or labrum may also break the tip of a conventional cannula. If the cannula is chipped during such a procedure, the result is a loose body of plastic floating around in the shoulder joint of the patient. The plastic must be removed and such removal can take a long time. It is not uncommon for a surgeon to spend an hour trying to locate and remove a small piece of transparent plastic. The patient must remain under anesthesia during such time. With a typical operating room costing about $60.00 per minute, an hour of searching causes an extra $3600.00 charge.

There is a need, therefore, for a cannula having a tip that will not break during surgery.

However, in view of the art considered as a whole at the time the present invention was made, it was not obvious to those of ordinary skill in this art how the identified needs could be met.

SUMMARY OF INVENTION

A cannula includes an elongate cannula body formed of a translucent or transparent polycarbonate plastic. The distal end of the cannula body has a sharp edge that frays and weakens sutures that rub against it. To protect sutures from such rubbing, a distal tip made of an unbreakable material is disposed in overlying, protective relation to the distal end of the cannula body and the sharp edge. The material may be a metal, a thermoplastic urethane or a thermoplastic urethane rubber. An annular recess formed in a lumen of the cannula body at the distal end of the cannula body accommodates the distal tip so that the lumen of the cannular body and the lumen of the distal tip are flush with one another.

An important object of the invention is to provide a cannula for use in surgical procedures that will not break upon encountering a bone or other hard object.

A closely related object is to provide a cannula having a protective distal tip secured to a distal end of the cannula body so that the distal tip absorbs the forces that would otherwise be applied to the distal end of the cannula body.

Another object is to provide a protective distal tip that has a lumen that lies flush with a lumen of the cannula body so that the protective distal tip does not obstruct surgical tools or implements that are fed through the lumen of the cannula body.

A more specific object is to provide a protective distal tip formed of thermoplastic urethane, thermoplastic urethane rubber, or a metallic material such as stainless steel.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1A:
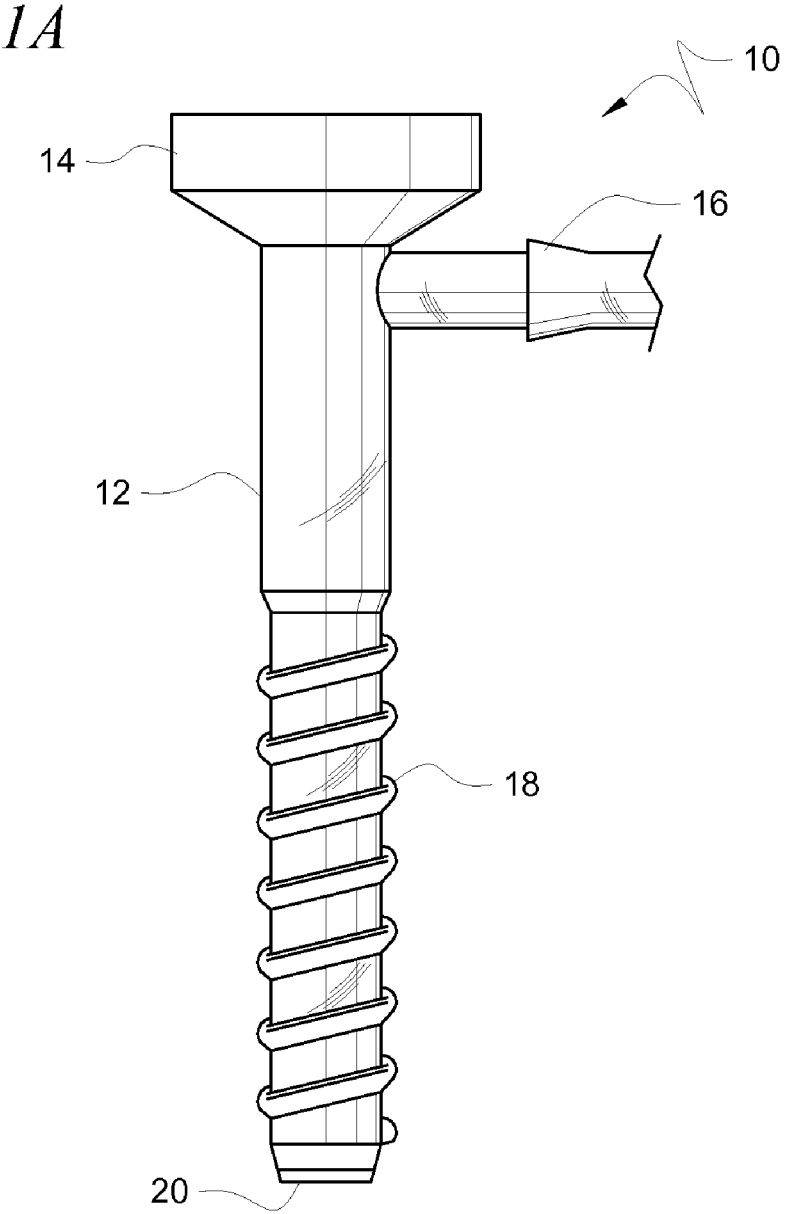
FIG. 1A is a side elevational view of the preferred embodiment.
Figure 1B:
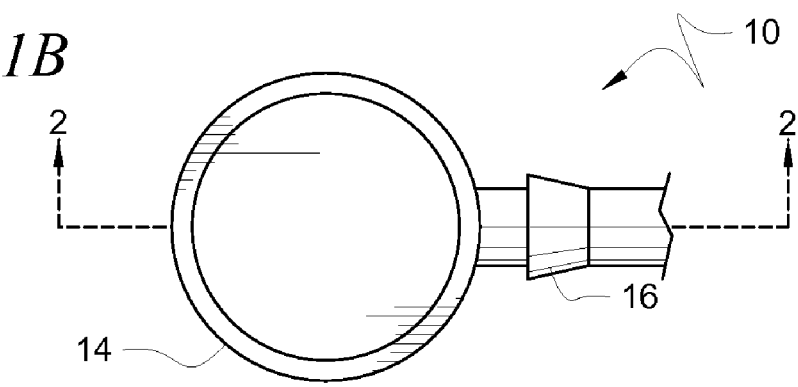
FIG. 1B is a top plan view thereof.

Referring now to FIGS. 1A and 1B, there it will be seen that an illustrative embodiment of the invention is denoted as a whole by the reference numeral 10.

Cannula 10 includes elongate cannula body 12 formed of a translucent or transparent polycarbonate plastic. Funnel-shaped head 14 is formed at the proximal end of cannula body 12 and port 16 extends radially from said cannula body. Helical threads 18 are formed in the leading half of cannula body 12. Head 14, port 16, and threads 18 are conventional and form no part of the invention, per se.

Cannula body 12 and threads 18 formed integrally therewith are preferably formed of polycarbonate.

Distal tip 20 overlies and protects the sharp distal end of cannula body 12. Said distal tip is preferably formed of thermoplastic urethane or thermoplastic urethane rubber.

The thermoplastic urethane structure of distal tip 20 acts like a windshield. It prevents the polycarbonate of which cannula body 12 is formed from chipping off and becoming a loose body.

In an alternative embodiment, distal tip 20 is formed of a metallic material such as stainless steel. Ceramics, glass, and other brittle materials cannot be used because they chip relatively easily.

A metal tip is advantageous not only because it will not break or chip during use, but also because it is visible under imaging means such as x-ray. This enables a surgeon to use the metal tip as a reference point if there is a need to retrieve a lost metal anchor or a piece of metal broken off from a surgical instrument.

Figure 2:
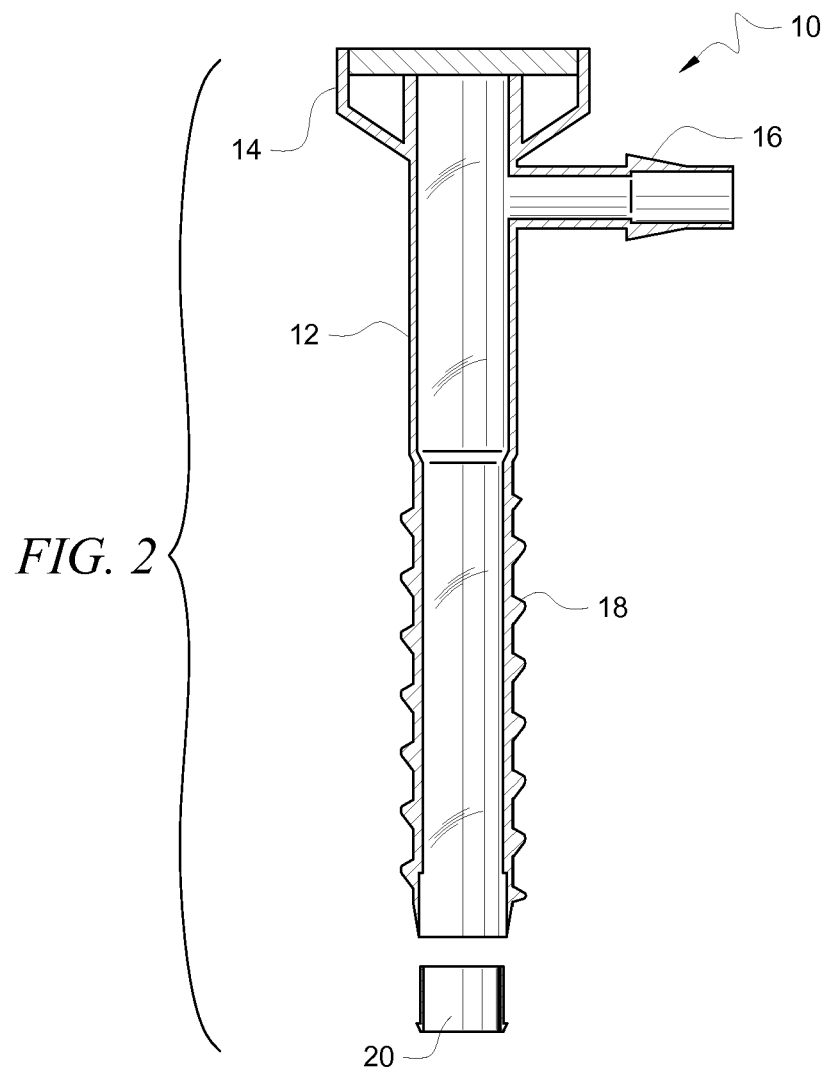
FIG. 2 is a sectional view taken along line 2-2 in FIG. 1, but modified into an exploded view.
Figure 3:
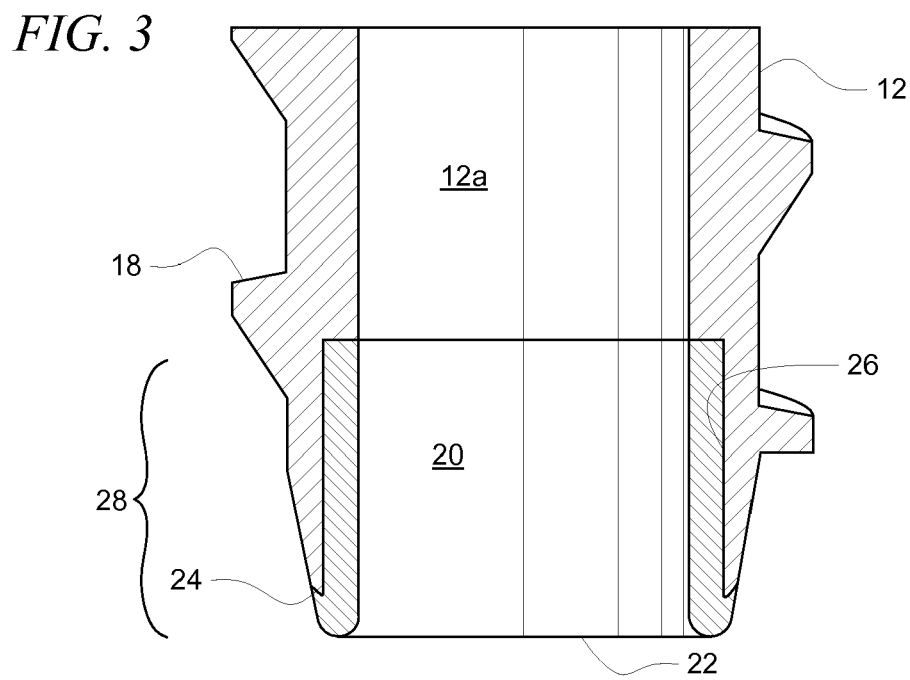
FIG. 3 is an enlarged view of the distal end of the structure depicted in FIG. 2.

The structure of distal tip 20 is more fully understood in connection with FIG. 2 and is best depicted in FIG. 3. Significantly, distal tip 20 has a rounded leading end 22 that covers sharp distal inner edge 24 of cannula body 12. Sharp distal inner edge 24 is uncovered in conventional cannulas and is responsible for fraying and breaking sutures that rub thereagainst. Distal tip 20 further includes a cylindrical main body.

Annular recess 26 is formed in the distal end of cannula body 12. Significantly, the lumen of distal tip 20 is flush with lumen 12a of cannula body 12. The internal diameter of recess 26 is substantially equal to the diameter of the cylindrical main body of distal tip 20. Rounded leading end 22 has a diameter slightly greater than the diameter of said cylindrical main body, as depicted in FIG. 3, so that it overlies sharp distal inner edge 24 of cannula body 12. The length of recess 26 is less than the longitudinal extent of distal tip 20 so that rounded leading end 22 of distal tip 20 extends slightly beyond leading end 24 of cannula body 12.

Sutures that rub against rounded leading end 22 will not fray or break.

Distal tip 20 is secured within recess 26 by any suitable means. In the preferred embodiment, an adhesive is used. The adhesive is preferably latex-free.

Due to the bond between distal tip 20 and annular recess 26, if cannula body 12 should break at any point within bracket 28 in FIG. 3, distal tip 20 will maintain its grip on said cannula body 12, preventing any chips from separating from said cannula body and entering into a surgical site as a free-floating body.

Moreover, the protection afforded by distal tip 20 not only prevents fraying of sutures and separation of chips. It also prevents sharp edge 24 from chipping.

The novel structure thus ensures that operation time will not be extended while a surgeon hunts for broken plastic chips from a cannula body, and that a second anchor and the associated expense will not be required during a procedure because sutures will not fray or break and no need for a second anchor will arise.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A cannula, comprising:
    a cannula body formed of a translucent or transparent polycarbonate plastic;
    said cannula body having a distal end and said distal end including a sharp edge that frays and weakens sutures that rub thereagainst;
    an annular recess formed in a lumen of said cannula body at said distal end of said cannula body;
    a distal tip disposed in overlying, protective relation to said distal end and said sharp edge, said distal tip having a cylindrical main body and a rounded leading end having a diameter slightly greater than a diameter of said cylindrical main body;
    said distal tip formed of a material that is substantially unbreakable upon contact with bone or other hard material encountered during surgery;
    said annular recess having a diameter substantially equal to a diameter of said cylindrical main body of said distal tip and said annular recess having a longitudinal extent substantially equal to a longitudinal extent of said cylindrical main body;
    said rounded leading end of said distal tip overlying said sharp edge of said distal end of said cannula body when said cylindrical main body is received within said annular recess; and
    said distal tip having a lumen flush with said lumen of said cannula body when said cylindrical main body of said distal tip is received within said annular recess.

2. The cannula of claim 1, further comprising:
    said material being a thermoplastic urethane.

3. The cannula of claim 1, further comprising:
    said material being a thermoplastic urethane rubber.

4. The cannula of claim 1, further comprising:
    said material being metallic.

5. The cannula of claim 4, further comprising:
    said material being stainless steel.

* * * * *